United States Patent
Carlson et al.

(10) Patent No.: US 11,158,412 B1
(45) Date of Patent: Oct. 26, 2021

(54) SYSTEMS AND METHODS FOR GENERATING PREDICTIVE DATA MODELS USING LARGE DATA SETS TO PROVIDE PERSONALIZED ACTION RECOMMENDATIONS

(71) Applicant: Grand Rounds, Inc., San Francisco, CA (US)

(72) Inventors: Eric Carlson, Boulder, CO (US); Ramakrishna Soma, Fremont, CA (US); Molong Li, San Francisco, CA (US); Jacob David Rifkin, San Francisco, CA (US); Zachary Taylor, Moraga, CA (US); Peyton Rose, San Francisco, CA (US)

(73) Assignee: GRAND ROUNDS, INC., San Francisco, CA (US)

( * ) Notice: Subject to any disclaimer, the term of this patent is extended or adjusted under 35 U.S.C. 154(b) by 0 days.

(21) Appl. No.: 17/077,441

(22) Filed: Oct. 22, 2020

(51) Int. Cl.
*G16H 20/00* (2018.01)
*G16H 10/60* (2018.01)
*G06N 20/00* (2019.01)
*G06K 9/62* (2006.01)

(52) U.S. Cl.
CPC ............ *G16H 20/00* (2018.01); *G06K 9/623* (2013.01); *G06K 9/6256* (2013.01); *G06N 20/00* (2019.01); *G16H 10/60* (2018.01)

(58) Field of Classification Search
CPC ........ G16H 10/60; G16H 20/00; G06N 20/00; G06K 9/623; G06K 9/6256
See application file for complete search history.

(56) References Cited

U.S. PATENT DOCUMENTS

| | | | |
|---|---|---|---|
| 2018/0182475 A1* | 6/2018 | Cossler | G16H 50/50 |
| 2018/0277246 A1* | 9/2018 | Zhong | A61B 5/486 |
| 2020/0005900 A1* | 1/2020 | Cha | G16H 50/20 |
| 2020/0051679 A1* | 2/2020 | Bostic | G16H 50/30 |
| 2020/0273373 A1* | 8/2020 | Grant | B33Y 50/00 |
| 2020/0275886 A1* | 9/2020 | Mason | A61B 5/7264 |

* cited by examiner

*Primary Examiner* — Michael Tomaszewski
*Assistant Examiner* — Jay M. Patel
(74) *Attorney, Agent, or Firm* — Finnegan, Henderson, Farabow, Garrett & Dunner, LLP

(57) ABSTRACT

Methods, systems, and computer-readable media for generating a personalized action recommendation are provided. The method acquires a request for a service that is associated with a user and the user's condition. The method then identifies one or more features of the user based on stored user information. The method next assigns the user to a segment based on the identified one or more features, generates a set of one or more recommended actions for the user based on the segment, and determines an expected value of each of the one or more recommended actions. The method determines a rank of the one or more recommended actions based on the expected value of each of the one or more recommended actions, and outputs a recommended action with a highest expected value for the user in response to the request for the service.

20 Claims, 9 Drawing Sheets

| Risk Assessments 710 | | | | |
|---|---|---|---|---|
| | Requests 720 | | | Observations 730 |
| | Request 721 | Group 722 | Notes 723 | Priority 724 | Status 725 |
| | Pharmacist referral | CCP | Low medication adherence | 1 | ✓ |
| | Eye exam | CCP | No valid eye exam in 12 months | 2 | ☐ |
| | PCP referral | CCP | Low quality PCP | 3 | ☐ |

Fig. 7B

| Risk Assessments 710 | Requests 720 | | Observations 730 | |
|---|---|---|---|---|
| | | | | ... |
| Observation 731 | Category 732 | | Notes 733 | |
| Low medication adherence | Medication adherence | | 70% PDC | |
| No valid eye exam in 12 months | Diabetes best practice | | Last eye exam on 1/1/2018 | |
| Low quality PCP | Provider quality | | Sanctioned provider | |

SYSTEMS AND METHODS FOR GENERATING PREDICTIVE DATA MODELS USING LARGE DATA SETS TO PROVIDE PERSONALIZED ACTION RECOMMENDATIONS

BACKGROUND

An ever increasing amount of data and data sources are now available to researchers, analysts, organization entities, and others. This influx of information allows for sophisticated analysis but, at the same time, present many new challenges for sifting through the available data and data sources to locate the most relevant and useful information in predictive modeling. As the use of technology continues to increase, so, too, will the availability of new data sources and information.

Analysis of large amounts of data can provide insights into the relationship between past and future events. Predictive models, built using historical data, can be applied to current data sets in an attempt to predict actions that could induce particular outcomes or events. To effectively predict actions, a model must identify specific data points or features that indicate that the predicted actions would cause the outcomes or events to occur. Because of the extensive amount of available data, however, determining which specific features of the existing data are relevant poses significant challenges. Additionally, different domains can have different relevant indicators.

Moreover, a predictive model must be generic enough to effectively apply to a wide variety of future data sets and, at the same time, specific enough to provide accurate prediction. Striking the balance between high model performance and generalizability to new data is especially challenging when there are many millions or billions of features and many different types of models that need to be built.

While current predictive models can be built using analysis, research, existing publications, and discussions with domain experts, this process can be resource and time intensive. Further, while the produced model may be effective for predicting actions to various users, the time and resources necessary to produce similar predictive models for many thousands of users may not be feasible. Therefore, there is a need for an improved system and method for accurate and efficient generation of predictive data models that can apply across domains and is capable of identifying specific features of existing data that can be most effectively used to predict personalized actions for users to cause a particular future event.

SUMMARY

Certain embodiments of the present disclosure relate to a non-transitory computer readable medium, including instructions that when executed by one or more processors cause a system to perform a method for generating a personalized action recommendation, the method comprising: acquiring a request for a service, wherein the request is associated with a user and the user's condition; identifying one or more features of the user based on stored user information; assigning the user to a segment based on the identified one or more features; generating a set of one or more recommended actions for the user based on the segment; determining an expected value of each of the one or more recommended actions; determining a rank of the one or more recommended actions based on the expected value of each of the one or more recommended actions; and outputting a recommended action with a highest expected value for the user in response to the request for the service.

In some embodiments, the expected value of each of the one or more recommended actions may be determined based on an expected value of resolving the user's condition, a probability that the one or more recommended actions resolves the user's condition, a probability that the user's condition is resolved without the one or more recommended actions, and a cost of taking the one or more recommended actions. In other embodiments, the expected value of each of the one or more recommended actions may be determined using a machine learning model. The machine learning model may comprise at least one of cohort matching or a regression model. The machine learning model may be trained using the stored user information.

In another embodiment, the one or more features may comprise a goal associated with the user, and the goal associated with the user may be extrapolated based on stored information associated with the user. In some embodiments, the segment may comprise a set of users who share at least one of the one or more features or the user's condition. In some embodiments, the stored user information may have been normalized using data from different data sources.

Certain embodiments of the present disclosure relate to a method performed by a system for generating a personalized action recommendation, the method comprising: acquiring a request for a service, wherein the request is associated with a user and the user's condition; identifying one or more features of the user based on stored user information; assigning the user to a segment based on the identified one or more features; generating a set of one or more recommended actions for the user based on the segment; determining an expected value of each of the one or more recommended actions; determining a rank of the one or more recommended actions based on the expected value of each of the one or more recommended actions; and outputting a recommended action with a highest expected value for the user in response to the request for the service.

In some embodiments, the expected value of each of the one or more recommended actions may be determined based on an expected value of resolving the user's condition, a probability that the one or more recommended actions resolves the user's condition, a probability that the user's condition is resolved without the one or more recommended actions, and a cost of taking the one or more recommended actions. In other embodiments, the expected value of each of the one or more recommended actions may be determined using a machine learning model. The machine learning model may comprise at least one of cohort matching or a regression model. The machine learning model may be trained using the stored user information.

In another embodiment, the one or more features may comprise a goal associated with the user, and the goal associated with the user may be extrapolated based on stored information associated with the user. In some embodiments, the segment may comprise a set of users who share at least one of the one or more features or the user's condition. In some embodiments, the stored user information may have been normalized using data from different data sources.

Certain embodiments of the present disclosure relate to a system for generating a personalized action recommendation. The system includes one or more processors executing processor-executable instructions stored in one or more memory devices to perform a method, the method comprising: acquiring a request for a service, wherein the request is associated with a user and the user's condition; identifying one or more features of the user based on stored user information; assigning the user to a segment based on the identified one or more features; generating a set of one or more recommended actions for the user based on the segment; determining an expected value of each of the one or more recommended actions; determining a rank of the one or more recommended actions based on the expected value of each of the one or more recommended actions; and outputting a recommended action with a highest expected value for the user in response to the request for the service.

BRIEF DESCRIPTION OF THE DRAWINGS

The accompanying drawings, which are incorporated in and constitute a part of this specification, illustrate several embodiments and, together with the description, serve to explain the disclosed principles. In the drawings:

FIG. 7B illustrates another exemplary user interface for providing personalized action recommendation, according to some embodiments of the present disclosure.

FIG. 7C illustrates another exemplary user interface for providing personalized action recommendation, according to some embodiments of the present disclosure.

DETAILED DESCRIPTION

In the following detailed description, numerous specific details are set forth in order to provide a thorough understanding of the disclosed example embodiments. However, it will be understood by those skilled in the art that the principles of the example embodiments may be practiced without every specific detail. Well-known methods, procedures, and components have not been described in detail so as not to obscure the principles of the example embodiments. Unless explicitly stated, the example methods and processes described herein are neither constrained to a particular order or sequence nor constrained to a particular system configuration. Additionally, some of the described embodiments or elements thereof can occur or be performed simultaneously, at the same point in time, or concurrently. Reference will now be made in detail to the disclosed embodiments, examples of which are illustrated in the accompanying drawings. Unless explicitly stated, sending and receiving as used herein are understood to have broad meanings, including sending or receiving in response to a specific request or without such a specific request. These terms thus cover both active forms, and passive forms, of sending and receiving.

The embodiments described herein provide technologies and techniques for evaluating vast amounts and types of data to allow for efficient creation of predictive models that can be used to recommend personalized actions for the user. These technologies can extract information from large and varied data sets, identify features associated with the user from the extracted information, and recommend, using predictive models, personalized actions for the user based on the identified features Further, the technologies and techniques herein can assign users to segments based on the identified features. Accordingly, the technologies can group users into segments based on one or more features or medical conditions that the users have in common.

These technologies can also use machine learning models to efficiently rank the personalized actions recommended for the user based on priority levels associated with each recommended action. Accordingly, the technologies can provide effective and accurate predictions that can be used to evaluate and recommend potential courses of action. The technologies and methods allow for the application of machine learning models to personalized circumstances. Accordingly, these methods and technologies allow for detailed evaluation and recommendation that can improve decision making on a case-by-case or user-by-user basis.

Figure 1:
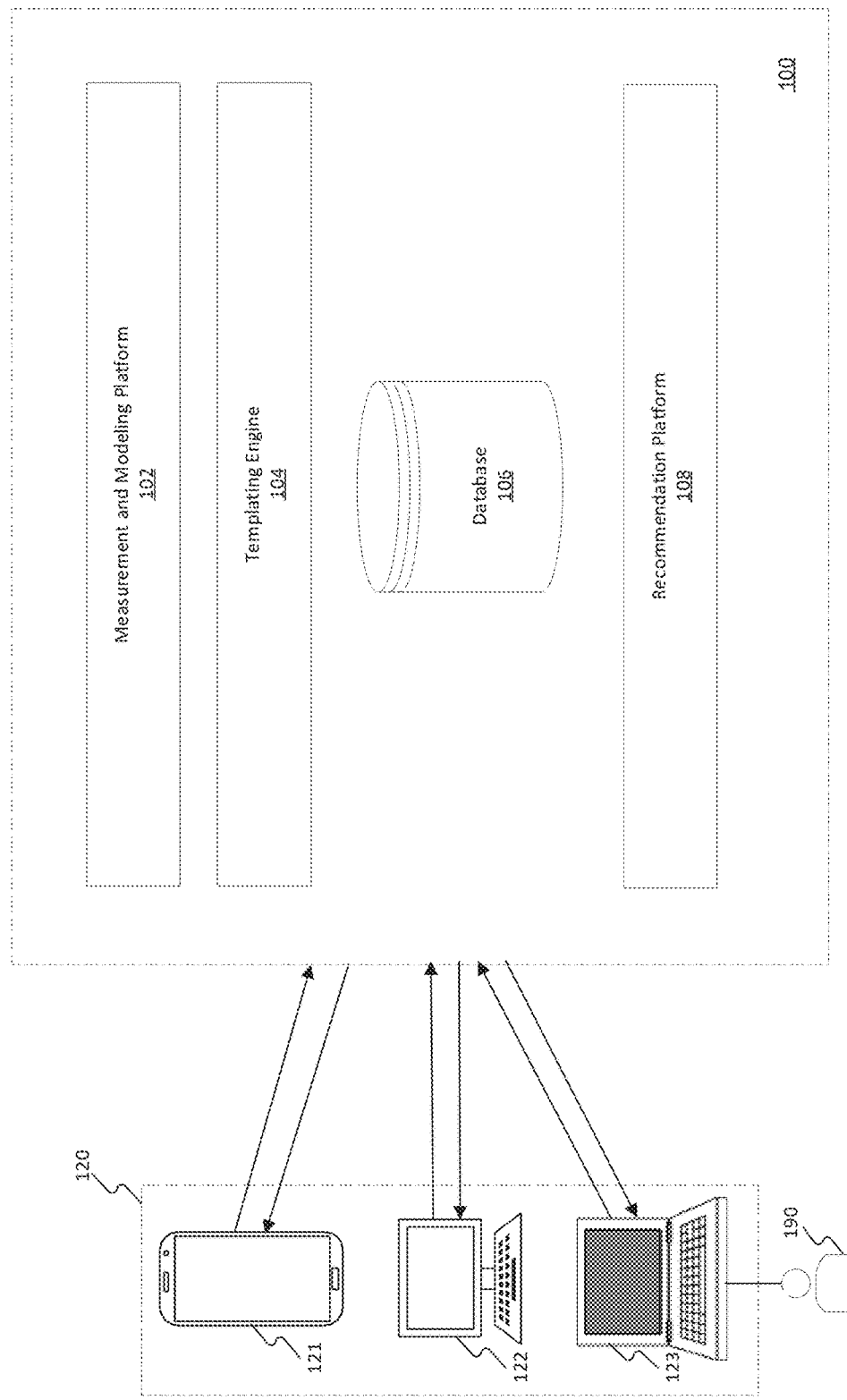
FIG. 1 is a block diagram showing various exemplary components of a system for generating a personalized action recommendation, according to some embodiments of the present disclosure.

FIG. 1 is a block diagram showing various exemplary components of a system 100 for generating a personalized action recommendation, according to some embodiments of the present disclosure. System 100 may comprise a measurement and modeling platform 102, a templating engine 104, a database 106, and a recommendation platform 108.

As illustrated in FIG. 1, devices 120 may comprise devices 121 (mobile device), 122 (desktop computer), and 123 (laptop). Users may communicate with system 100 using devices 120. For example, a user 190 of device 123 may send a query to system 100. User 190 may, for example, comprise at least one of a marketer, a patient, a care coordinator, or a clinician. The query received by system 100 may result in measurement and modeling platform 102, templating engine 104, database 106, and recommendation platform 108 working together to generate a personalized action recommendation. After receiving the query, system 100 may convert the query to a service request in order to generate a personalized action recommendation. In some embodiments, the query sent by devices 120 may include a service request.

The system 100 may comprise a measurement and modeling platform 102 to receive information associated with a user from one or more sources. This information associated with the user may be normalized using data from different data sources. For example, this information can be healthcare data and information, which may comprise medical records associated with the user, the user's medical conditions, the user's medication adherence information, the user's medical goals, the user's attributes, the user's behaviors, the user's gap in care, the user's medications, social determinants of health associated with the user, or any other information associated with the user that can be used to recommend actions to resolve the user's medical conditions. Healthcare data and information associated with the user may be based on an insurance provider's inferences, a clinician's observations, statements directly from the user, or the like. Additionally or alternatively, healthcare data and information associated with the user may include observations that are learned or inferred about the user based on information from one or more data sources.

In some embodiments, measurement and modeling platform 102 may be configured to identify one or more features of the user based on stored data and information associated with the user. For example, upon receiving a service request from the user, measurement and modeling platform 102 may be configured to identify one or more features associated with the user. Features may comprise, by way of example, a state of the user, such as a gap in care, a medical condition, genetics data, medications, attributes, behaviors, or social determinants of health associated with the user. Features may also comprise an identify of the user, such as a marketer, a patient, an insurance provider, a care coordinator, or a clinician. Additionally or alternatively, features may comprise a goal associated with the user. A goal associated with the user may be extrapolated based on stored medical history of the user. Features may also include risk features associated with the user, such as Charlson Comorbidity Index, Hierarchical Condition Categories (HCC), Clinical Classifications Software (CCS), or the like. In addition, features may also include current or past medical episodes associated with the user.

In some embodiments, measurement and modeling platform 102 may be configured to assign the user to a segment based on the identified features associated with the user. In particular, measurement and modeling platform 102 may be configured to groups users into various segments based on features associated with each user and assign one or more segmentation tags to each user. Accordingly, instead of generating a personalized recommended action for each specific user, system 100 may be able to generate a personalized recommended action for each segment of users sharing common features or conditions. By way of example, measurement and modeling platform 102 may implement a one or more segmentation models to segment users based on common features or conditions. A segmentation model may be configured to generate classification of a user to a segment or a segmentation class. The segmentation model may also be configured to determine a confidence value of the classification and generate an explanation for the classification for reference. Additionally or alternatively, the segmentation model may also be configured to determine a severity score for each classification. The segmentation model may comprise a rule-based model or a machine-learning-based model. By way of example, the segmentation model may create segments and assign users to segments based on rules (e.g., matching) procedure using diagnosis codes, features associated with users, episodes associated with the user, or the like. In other embodiments, the segmentation model may use machine learning models to generate segments and assign users to segments. For example, segmentation model may consider genetics data of the users, as certain types of treatments may be more effective for a user having a certain genetic profile as opposed to another.

In some embodiments, the measurement and modeling platform 102 may implement a utilization model in order to compute the likelihood of utilization (i.e., adherence) of a user to a recommended action. The utilization model may be configured to compute the likelihood of utilization based on stored healthcare data and information associated with the user. The utilization model may also be configured to determine the likelihood of utilization for each segment of users, rather than computing the likelihood of utilization for each user. The utilization model may be a rule-based model or a machine-learning-based model.

In some cases, a user may be assigned to multiple segments based on the features associated with the user. Accordingly, the measurement and modeling platform 102 may implement an aggregation model to aggregate the multiple segments, to which the user is assigned, into a single, cohesive view of the user. The aggregation model may be a rule-based model or a machine-learning-based model. In some embodiments, the aggregation model may aggregate the multiple user-segment assignments as a batch step. In some embodiments, the aggregation model may aggregate the multiple user-segment assignments daily or more frequently to update the segmentation tags associated with the user.

The system 100 may also include a templating engine 104 configured to provide an analytics interface to develop quality measurements. The templating engine 104 may combine information associated with the user, features associated with the user, or segments associated with the user from measurement and modeling platform 102 with templates in order to generate analytics interface for the users. The analytics interface may be provided to the user via documents, web pages, source codes, mobile application interface, or the like.

The system 100 may also include a database 106 to help generate a personalized recommended action in response to the user's service request. By way of example, database 106 may be configured to store normalized information associated with the user to help generate the personalized recommended action. For example, information associated with the user that is stored in database 106 may include user's medical records, user's past usage of system 100, user's preferences, features associated with the user, segment assignments associated with the user, or the like. Database 106 may also be configured to store one or more models used by measurement modeling platform 102 to generate the personalized recommended action, including but not limited to, segmentation models, aggregation models, and utilization models. Database 106 may also be configured to store information about the previous queries or service requests sent to system 100 by the user.

Database 106 may include, for example, Oracle™ databases, Sybase™ databases, or other relational databases or non-relational databases, such as Hadoop™ sequence files, HBase™, or Cassandra™. Database 106 may include computing components (e.g., database management system, database server, etc.) configured to receive and process requests for data stored in memory devices of the database(s) and to provide data from the database(s). Database 106 may include NoSQL databases such as HBase, MongoDB™ or Cassandra™. Alternatively, database 106 may include relational databases such as Oracle, MySQL and Microsoft SQL Server. In some embodiments, database 106 may include Amazon S3. In some embodiments, database 106 may take the form of servers, general purpose computers, mainframe computers, or any combination of these components.

In some embodiments, system 100 may further include a recommendation platform 108. Recommendation platform 108 may be configured to generate a set of one or more recommended actions for the user in response to the user's service request based on features associated with the user and segments to which the user is assigned. The one or more actions may be recommended for the user to help resolve the user's conditions or needs. By way of example, the one or more recommended actions may include recommending a new medication for the user, recommending or scheduling a medication review for the user, recommending or scheduling a physical exam or a doctor's visit for the user, sending an email to the user to engage the user, or any action to help the user resolve the user's conditions or needs. The recommendation platform 108 may also be configured to identify high risk users (e.g., users with conditions or needs that require urgent attention). The recommendation platform 108 may be configured to prioritize high risk users and generate personalized recommended actions for users based on their priority level. As discussed below, when there are multiple recommended actions generated for the user based on the one or more segments associated with the user, the recommendation platform 108 may be configured to rank the multiple recommended actions by determining an expected value of each of the recommended actions (e.g., from highest expected value to lowest expected value). The expected value may be determined based on an expected value of resolving the user's condition, a probability that the one or more recommended actions resolves the user's condition, a probability that the user's condition is resolved without the one or more recommended actions, and a cost of taking the one or more recommended actions. Additionally or alternatively, the expected value of each recommended action may be determined using a machine learning model, such as cohort matching or a regression model. The machine learning model used to determine the expected value of each recommended action may be trained using healthcare data and information associated with users that are stored, for example, in database 106.

System 100, upon receiving the query or the service request from the user, may identify the relevant user details from database 106 containing user information. In some embodiments, the recommendation platform 108 may recommend a list of service providers who can help resolve the user's query or service request. The service request received by system 100 and healthcare data and information stored in database 106 may be used in identifying the service providers to recommend to the user to resolve the user's conditions or needs. In some embodiments, the recommendation platform 108 may provide lists of service providers for the user. For example, the recommendation platform 108 may behave as a meta-search engine offering results from several search engine systems, with each having their own subset of search results, including service providers.

The healthcare data and information about a user from database 106 may help update the user's service request to include additional services or specify further filters on a service identified as part of the service request. For example, in one scenario, the user may have preferences set in the user preferences stored in database 106 for service providers available over the weekend and having certain language skills. In another scenario, system 100 may update the user's service request based on features associated with the user to include an additional request (e.g., for a different specialist) based on past health care information stored in database 106.

The service request made by the user, in another example, may only mention a general query and not mention a specific service. For example, the user may send a query for a foot pain symptom. Based on the health record information present in database 106, the recommendation platform 108 may generate a recommendation to see a physiotherapist after identifying that the user has recently undergone a knee replacement surgery.

System 100 can be related to many different domains or fields of use. Descriptions of embodiments related to specific domains, such as healthcare, is not intended to limit the disclosed embodiments to those specific domains, and embodiments consistent with the present disclosure can apply to any domain that utilizes predictive modeling based on available user information.

Figure 2:
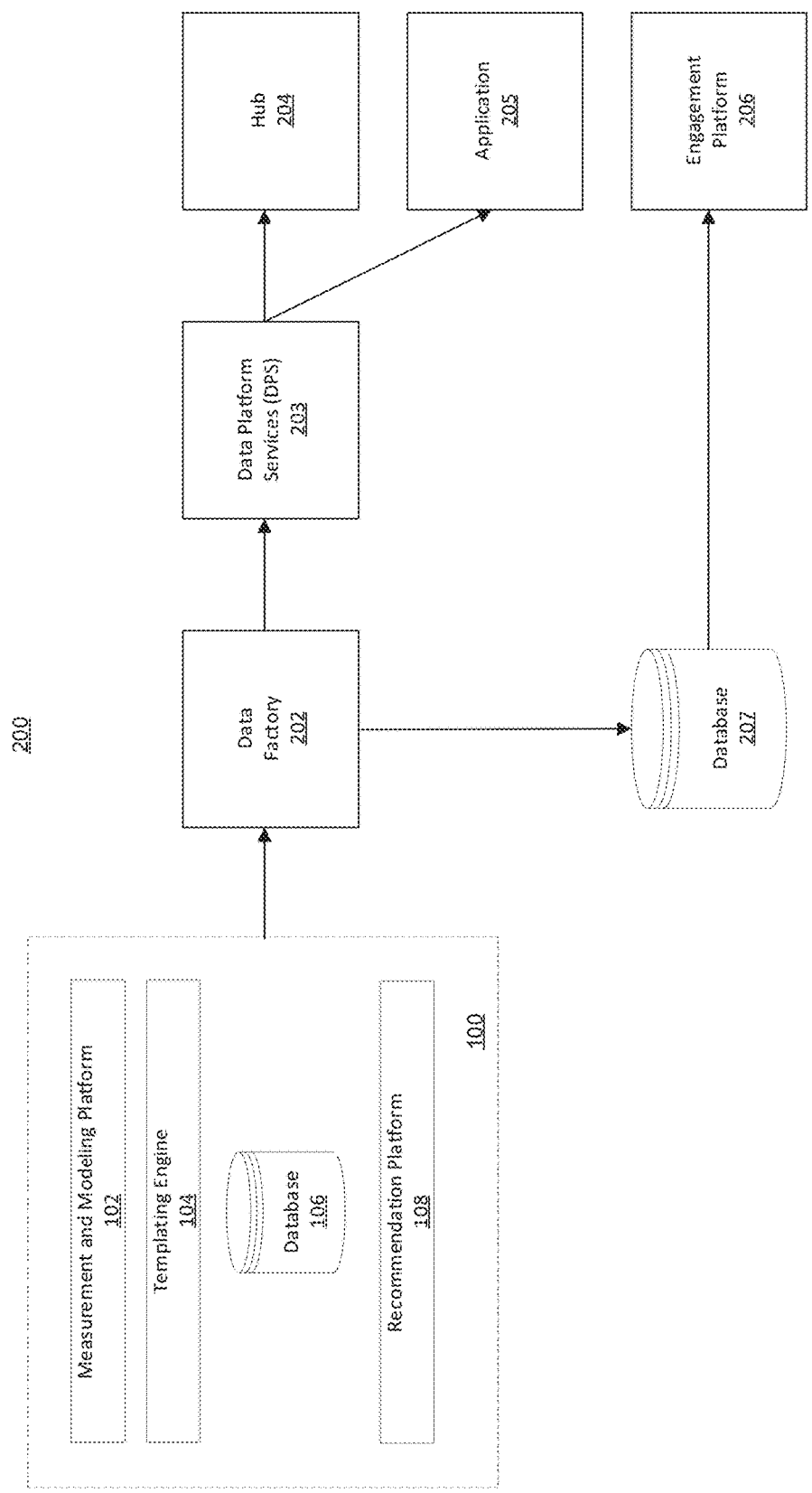
FIG. 2 is a schematic diagram showing various exemplary components of a system for generating a personalized action recommendation, according to some embodiments of the present disclosure.

FIG. 2 is a schematic diagram of an exemplary system 200 for generating personalized recommended actions, according to some embodiments of the present disclosure. As shown in FIG. 2, system 200 may comprise the system 100 of FIG. 1, data factory 202, data platform services (DPS) 203, hub 204, mobile or web application 205, engagement platform 206, and database 207.

Figure 4:
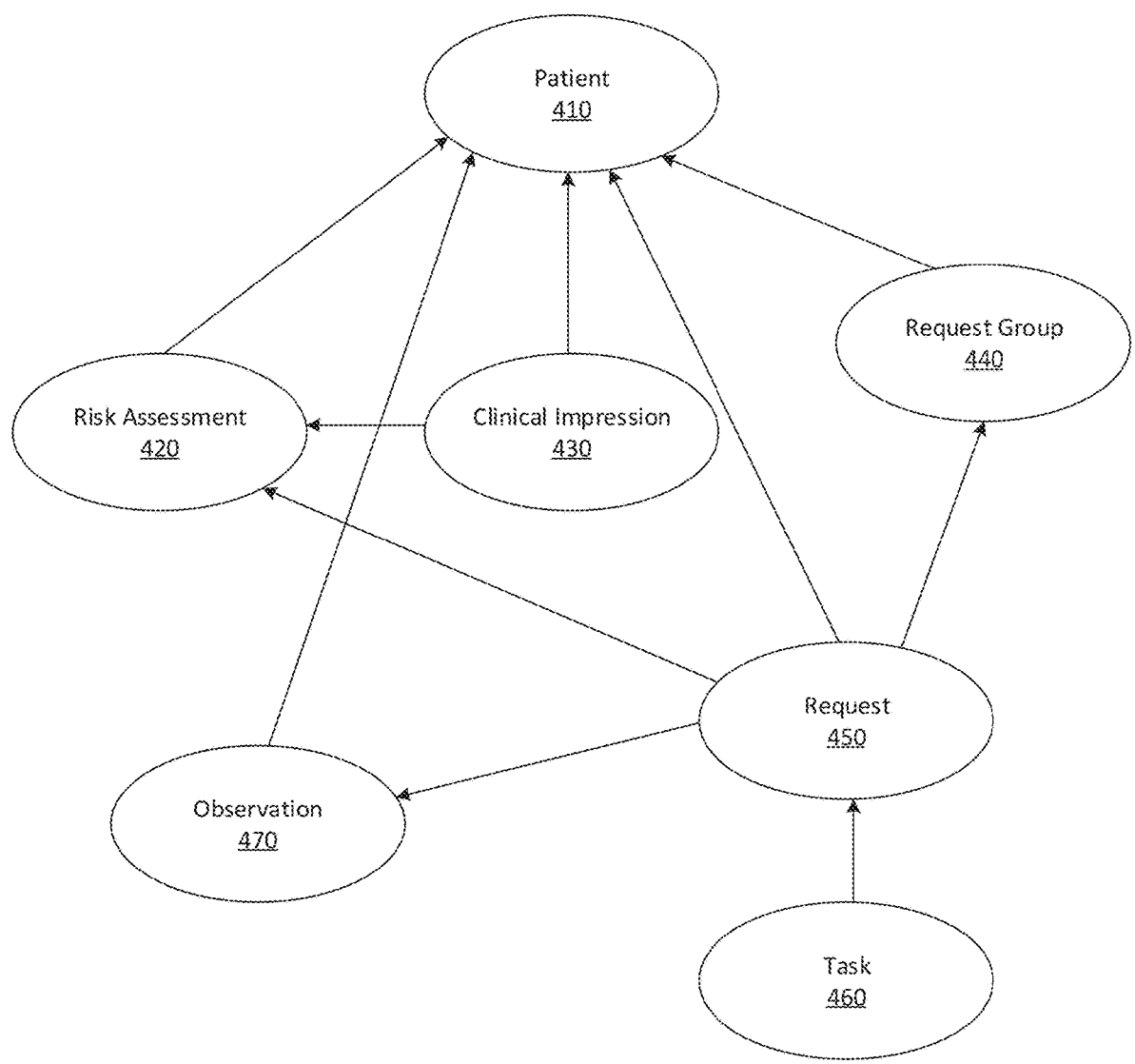
FIG. 4 illustrates an exemplary interoperability resources bundle used to generate a personalized action recommendation, according to some embodiments of the present disclosure.

As shown in FIG. 2, system 200 may include a data factory 202. Data factory 202 may be a cloud-based data integration service configured to integrate and manage healthcare data and information associated with users. In some embodiments, data factory 202 may integrate healthcare data and information associated with users into Fast Healthcare Interoperability Resources (FHIR) models or bundles. By way of example, as seen in FIG. 4, data factory 202 may integrate healthcare data and information associated with each user, such as patient 410, into a respective FHIR bundle 400. FHIR bundles generated for users may be stored in data factory 202. Additionally or alternatively, FHIR bundles generated for users may be stored in database 207.

Referring back to FIG. 2, system 200 may further include data platform services (DPS) 203. DPS 203 may comprise a cloud-based serving layer configured to provide application programming interface (API) access to FHIR bundles managed by data factory 202 in order to feed hub 204 or mobile application 205 so as to output personalized action recommendations to users. DPS 203 may comprise, for example, Amazon S3. DPS 203 may be configured to process, integrate, ingest, and store FHIR bundles associated with users such that hub 204 or mobile application 205 can access the FHIR bundles to display personalized recommended actions for users.

When system 200 receives a request for service from a user, for example, hub 204 may access FHIR resources or bundles from DPS 203, ingest FHIR resources or bundles, and index them for immediate query and search. Accordingly, hub 204 may be configured to provide consistent, real-time view of healthcare data and information for users, including personalized recommended actions for users. Additionally or alternatively, users may access healthcare data and information, as well as personalized action recommendations via mobile application 205. Mobile application 205 may refer to a software application that the users may access via their mobile device, such as mobile device 121 of FIG. 1. Users, for example, may access healthcare data and information, including but not limited to features associated with users, segments associated with users, insights, preferences, and personalized action recommendations.

System 200 may further include engagement platform 206. Engagement platform 206 may comprise a software application configured to build, scale, and control marketing campaigns across various channels that engage users. For example, engagement platform 206 may be configured to control campaigns for inbound or outbound user engagement across channels, such as phone calls, e-mails, mobile notifications, push notifications, or the like.

In some embodiments, system 200 may include database 207. Although FIG. 2 illustrates one database 207, system 200 may comprise two or more databases. Database 207 may be configured to store information associated with users. For example, database 207 may be configured to store FHIR bundles associated with users, FHIR resources, FHIR flat projections, or the like. Database 207 may include, for example, Oracle™ databases, Sybase™ databases, or other relational databases or non-relational databases, such as Hadoop™ sequence files, HBase™, or Cassandra™. Database 207 may include computing components (e.g., database management system, database server, etc.) configured to receive and process requests for data stored in memory devices of the database(s) and to provide data from the database(s). Database 207 may include NoSQL databases such as HBase, MongoDB™ or Cassandra™. Alternatively, database 207 may include relational databases such as Oracle, MySQL and Microsoft SQL Server. In some embodiments, database 207 may include Amazon S3. In some embodiments, database 207 may take the form of servers, general purpose computers, mainframe computers, or any combination of these components.

Figure 3:
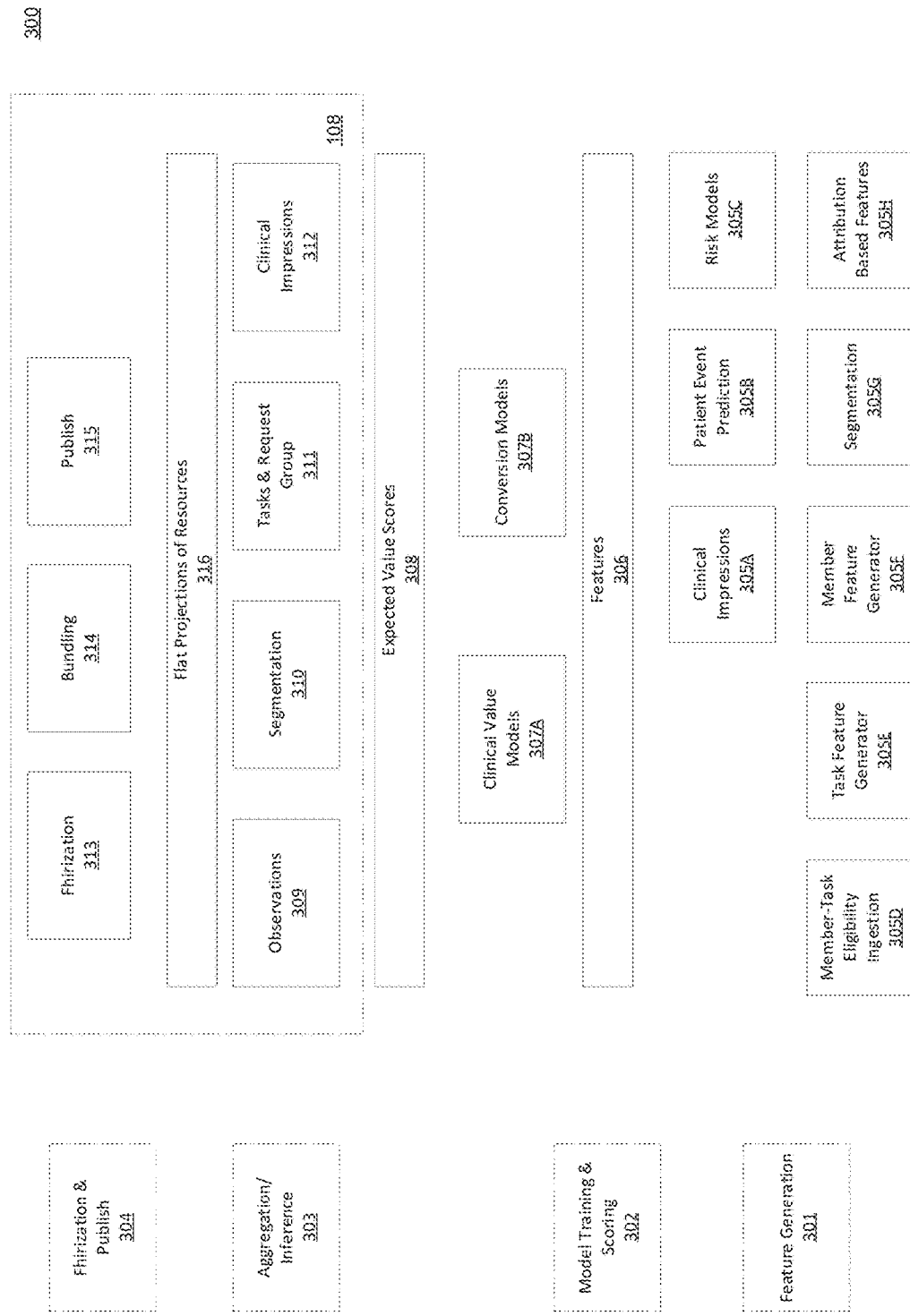
FIG. 3 is another block diagram showing various exemplary components of a system for generating a personalized action recommendation, according to some embodiments of the present disclosure.

FIG. 3 illustrates another block diagram showing various exemplary components of a system 300 for generating a personalized action recommendation, according to some embodiments of the present disclosure. System 300 for generating personalized action recommendations may comprise various components, including feature generation 301, model training and scoring 302, aggregation/inference 303, and fhirization and publishing 304. Each component of system 300 may be responsible for generating and providing a personalized action recommendation for a user.

In some embodiments, feature generation 301 component of system 300 may be responsible for identifying features associated with a user, such as user 190, upon receiving a request for a service. Feature generation 301 component, for example, may acquire clinical impressions 305A associated with the user, patient event prediction 305B associated with the user, risk models 305C to identify risks associated with the user, member-task eligibility ingestion 305D associated with the user, task features 305E, member features 305F, segmentation information 305G, and attribution based features 305H associated with the user.

Clinical impressions 305A associated with the user may comprise a record of a clinical assessment performed to determine one or more conditions that may affect the user. Patient event prediction 305B may comprise rule-based or machine learning models to predict events associated with the user, such as diagnosis, therapy initiation, progression, or discontinuation. Risk models 305C may comprise rule-based or machine learning models that may be used to identify or predict risks associated with the user.

In some embodiments, various features associated with the user may be acquired in the feature generation 301 component. Member-task eligibility ingestion 305D may comprise information associated with whether the user may be eligible for various medical tasks performed to resolve the user's conditions or needs. For example, member-task eligibility ingestion 305D may comprise insurance coverage features associated with the user. In addition, task features 305E may be acquired, which may comprise features associated with activities that can be performed on behalf of the user in order to allow the user to undertake or perform a recommended action. Member features 305F may comprise features associated with the user, including but not limited to a state of the user, such as a gap in care, a medical condition, genetics data, medications, attributes, behaviors, or social determinants of health associated with the user. Member features 305F may also comprise an identity of the user, such as a marketer, a patient, an insurance provider, a care coordinator, or a clinician. Additionally or alternatively, member features 305F may comprise a goal associated with the user. A goal associated with the user may be extrapolated based on stored medical history of the user. Features may also include risk features associated with the user, such as Charlson Comorbidity Index, Hierarchical Condition Categories (HCC), Clinical Classifications Software (CC S), or the like. Additionally or alternatively, segmentation information 305G associated with the user may be obtained in order to identify segments, to which the user belongs. Moreover, attribution-based features 305H associated with the user may be obtained, including but not limited to, behaviors or social determinants of health associated with the user.

After obtaining various information and features associated with the user in the feature generation 301 component, the features associated with the user may be organized into a repository of features 306. All of the features 306 associated with the user may be input into clinical value models 307A or conversion models 307B in the model training and scoring 302 component of system 300. Clinical value models 307A may determine whether certain recommended actions may help in resolving conditions or needs associated with the user. Clinical value models 307A, for example, may consider the risk status and health information associated with the user, costs of fulfilling recommended actions, the user's satisfaction with the recommended action, benefits reaped by the user for taking the recommended action, or clinical outcomes as a result of the user taking the recommended action. Conversion models 307B may determine attitudes or behaviors of the user with respect to the recommended action. For example, if the recommended action is getting a medication review, conversion model 307B may determine whether the user may find the medication review helpful in resolving the user's problems with medication adherence. The results of clinical value models 307A or conversion models 307B may be used to determine an expected value score 308 of a recommended action for the user. As discussed in more detail below, the expected value score 308, for example, may be determined based on an expected value of resolving the user's condition, a probability that the one or more recommended actions resolves the user's condition, a probability that the user's condition is resolved without the one or more recommended actions, and a cost of taking the one or more recommended actions. In some embodiments, the expected value of resolving the user's condition may be determined by subtracting an expected cost of care if the user's condition is resolved from an expected cost of care if the user's condition is not resolved.

After calculating the expected value scores 308 of recommended actions, the aggregation/inference 303 component of system 300 may gather observations 309 associated with the user, segmentation information 310 associated with the user, tasks and request group 311 associated with the user, and clinical impressions 312 associated with the user to determine flat projections of resources 316. Observations 309 may comprise information about the user that can be learned or inferred from, for example, healthcare data and information associated with the user. Observations 309 may be mapped to measurements, test results (e.g., biometrics), or medical records associated with the user and may be indicative of conditions or needs associated with the user. Segmentation information 310 may be the same as segmentation information 305G associated with the user. Segmentation information 310 may refer to segments, to which the user belongs, based on common features, conditions, or needs that the user shares with other members. Task and request group 311 associated with the user may refer to activities that can be performed on behalf of the user in order to allow the user to undertake or perform a recommended action. Tasks may also be linked to observations 309. For example, certain tasks may need to be performed based on certain observations 309 associated with the users. Request group, for example, may comprise one or more end-users who act on a set of tasks for the user. Each request group may be linked to and associated with a ranked set of tasks for the user. Clinical impressions 312 may be the same as clinical impressions 305A associated with the user. Accordingly, clinical impressions 312 may comprise a record of a clinical assessment performed to determine one or more conditions that may affect the user. Based on observations 309 associated with the user, segmentation information 310 associated with the user, tasks and request group 311 associated with the user, and clinical impressions 312 associated with the user, recommendation platform 108 of system 300 may determine flat projections of resources 316 configured to determine the amount of resources that are needed in order to resolve the conditions or needs of the user. In some embodiments, flat projections of resources 316 may be stored in a database, such as database 207.

In some embodiments, system 300 may comprise a fhirization and publishing 304 component configured to aggregate information associated with the user into FHIR bundles and publish (e.g., output or display) recommended actions for the user. Fhirization 313 may comprise, for example, aggregating health data and information associated with the user such that healthcare data and information associated with the user is readily available, discoverable, and understandable. Bundling 314 may comprise storing healthcare data and information associated with the user into FHIR bundles, such as FHIR bundle 400 such that the hub 204 or mobile application 205 may easily access healthcare data and information associated with the user. Publishing 315 may refer to outputting or displaying healthcare data and information to the user. For example, publishing 315 may refer to the hub 204 or mobile application 205 accessing healthcare data and information associated with the user and outputting or displaying the information to the user. Publishing 315 may also refer to outputting or displaying personalized recommended actions to the user via hub 204 or mobile application 205.

As discussed above, FIG. 4 illustrates an exemplary FHIR bundle 400 used to generate a personalized action recommendation, according to some embodiments of the present disclosure. FHIR bundle 400 for each user, such as patient 410, may map various information associated with the user. For example, as shown in FIG. 4, FHIR bundle 400 for patient 410 comprise map risk assessment 420 associated with patient 410, clinical impression 430 of patient 410, request group 440 associated with patient 410, action 450 recommended to patient 410, observations 470 associated with patient 410, and tasks 460 associated with patient 410.

Risk assessment 420 may refer to any index or tool that is used to predict a general health status of patients who may have one or more comorbid conditions. Risk assessment 420 may comprise, for example, Charlson Comorbidity Index, Hierarchical Condition Categories (HCC), or Clinical Classifications Software (CCS) associated with patient 410. In some embodiments, clinical impressions 430 associated with patient 410 may comprise a record of a clinical assessment performed to determine one or more conditions that may affect patient 410. Risk assessment 420 associated with patient 410 may be based on an investigation of clinical impressions 430. Observations 470 may refer to information about patient 410 that can be learned or inferred from, for example, healthcare data and information associated with the user. Observations 470 may be mapped to measurements, test results (e.g., biometrics), or medical records associated with the user and may be indicative of conditions or needs associated with patient 410.

In some embodiments, FHIR bundle 400 may include information associated with a request group 440 associated with patient 410. Request group 440, for example, may comprise one or more end-users who act on a set of tasks for patient 410. Each request group 440 may be linked to and associated with a ranked set of tasks 460 for members assigned to request group 440. Tasks 460 may refer to activities that can be performed on behalf of patient 410 in order to allow patient 410 to undertake or perform a recommended action. Tasks 460 may also be linked to observations 470. For example, certain tasks 460 may need to be performed based on certain observations 470 associated with the users. In some embodiments, a combination of task 460 associated with patient 410 and request group 440 associated with patient 410 may determine an action 450 recommended to patient 410. As such, action 450 recommended to patient 410 may be based on a combination of various information associated with patient 410, including but not limited to observations 470, request group 440, task 460, and features associated with patient 410. Accordingly, hub 204 or mobile application 205 may access FHIR bundle 400 associated with patient 410 in order to output a personalized action recommendation in response to a request for service received from patient 410.

Figure 5:
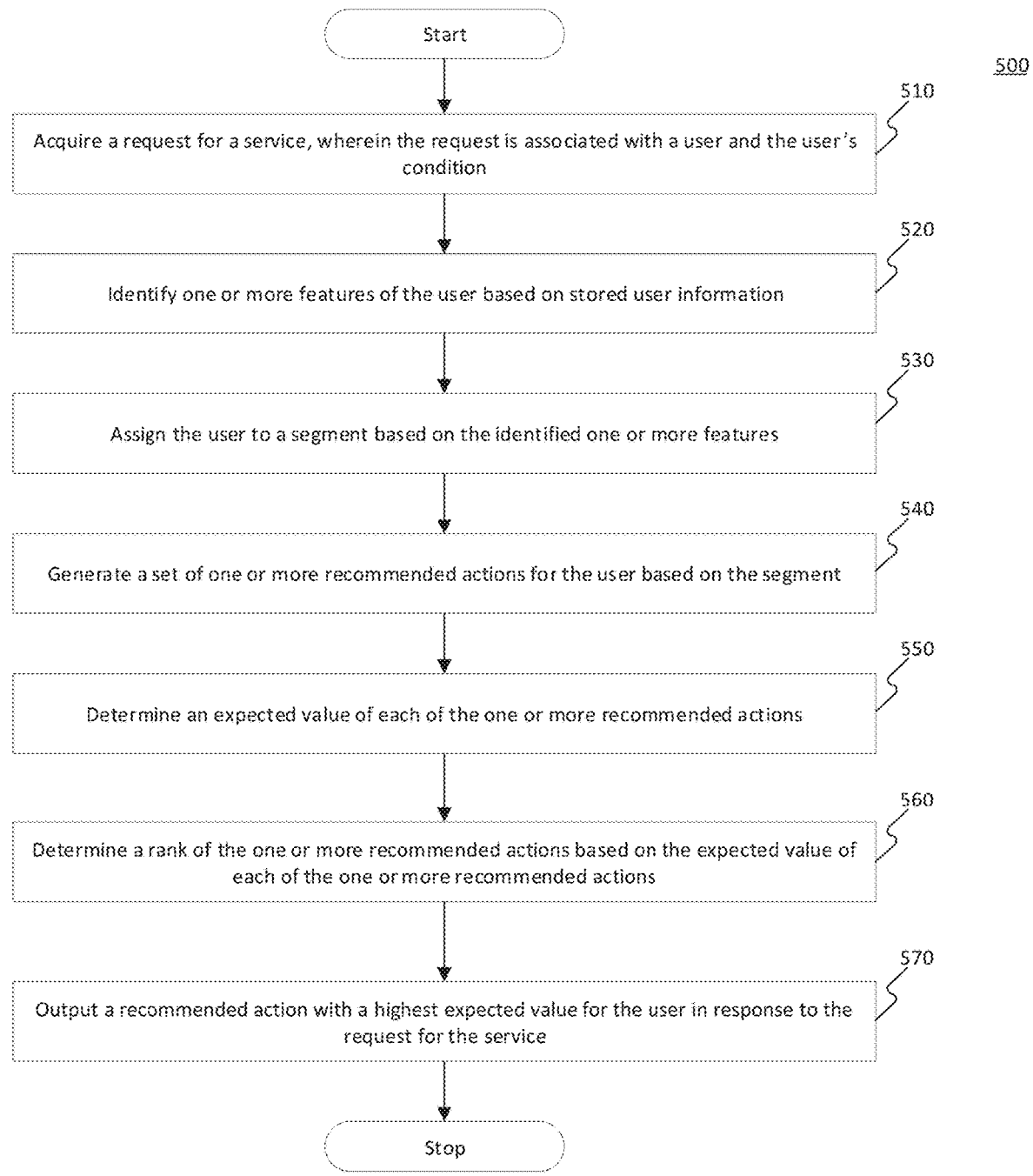
FIG. 5 is a flowchart showing an exemplary method for generating a personalized action recommendation, according to some embodiments of the present disclosure.

Referring now to FIG. 5, a flowchart showing an exemplary method 500 for generating a personalized action recommendation, according to some embodiments of the present disclosure, is provided. The steps of method 500 may be performed by one or more processors of system 100 for purposes of illustration. It will be appreciated that the illustrated method 500 can be altered to modify the order of steps and to include additional steps.

In step 510, one or more processors of system 100, such as one or more processors of measurement and modeling platform 102, may acquire a request for a service. For example, when user 190 sends a query or a service request via one or more device 120, one or more processors of system 100 may acquire the request from user 190. The request may be associated with user 190 and a condition or need associated with user 190. For example, the request may be a request for medication review, a request for clinician referral, or the like. In some embodiments, the request for the service may be from a second user, who is different from the user, such as user 190. For example, the user, such as user 190, may be a patient, and the request for the service may be from a second user comprising at least one of a marketer, a care coordinator, or a clinician. Accordingly, a marketer, a care coordinator, or a clinician may send a request for a service for a patient. In other embodiments, the user may be a patient, and the user may send his or her own request for a service.

After acquiring the service request from user 190, method 500 may proceed to step 520. In step 520, one or more processors of system 100 may identify one or more features of user 190 based on the stored user information. For example, as discussed above, database 106 may store healthcare data and information associated with user 190. Database 106 may also store features associated with user 190 that are determined based on healthcare data and information associated with user 190. One or more processors of system 100, such as one or more processors of measurement and modeling platform 102, may identify one or more features of user 190 from database 106.

In some embodiments, the one or more features may comprise a state of user 190, and the state of user 190 may comprise at least one of a gap in care, a medical condition, medications, attributes, behaviors, genetics data, or social determinants of health associated with user 190. In other embodiments, the one or more features may comprise an identity of user 190, and the identity of user 190 may comprise at least one of a marketer, a patient, a care coordinator, or a clinician. In yet another embodiment, the one or more features may comprise a goal associated with user 190, and the goal associated with user 190 may be extrapolated based on stored medical history of user 190.

After identifying one or more features of user 190, method 500 may proceed to step 530. In step 530, one or more processors, such as one or more processors of measurement and modeling platform 102, may assign user 190 to a segment based on the one or more features. In some embodiments, the segment may comprise a set of users who share at least one of the one or more features associated with user 190. In some embodiments, user 190 may be assigned to multiple segments depending on the one or more features associated with user 190.

Method 500 may proceed to step 540, in which one or more processors, such as one or more processors of recommendation platform 108, may generate a set of one or more recommended actions for user 190 based on the segment, to which user 190 is assigned. For example, each segment may be pre-mapped to a set of recommended actions based on the user features associated with each segment. Accordingly, when user 190 is assigned to a particular segment based on the one or more identified features associated with user 190, one or more processors may generate a set of recommended actions for user 190 that are associated with the particular segment.

In some cases, user 190 may be assigned to multiple segments. Additionally or alternatively, there may be a plurality of recommended actions associated with each segment, to which user 190 is assigned. Accordingly, method 500 may proceed to block 550. In step 550, one or more processors, such as one or more processors of recommendation platform 108, may determine an expected value of each of the recommended actions in order to prioritize recommended actions with higher expected values. The expected value (EV) of each recommended action may be determined based on the following equation:

$$EV_{action, user} = \sum_{conditions} \{EV_{condition, user} * [P(\text{need} | \text{action, user}) - P(\text{need} | \text{no action, user})]\} - C_{action}$$

where $EV_{action, user}$ is the expected value of the recommended action specific to the user, such as user 190, $EV_{condition, user}$ is the expected value of resolving the user's condition, P(need|action, user) is the probability that the recommended action ultimately results in the user's condition being resolved (e.g., probability of the user completing any task recommended by the action (conversion), and probability that tasks recommended by the action resolve the user's condition (effectiveness)), P(need|no action, user) is the probability that the user's condition is resolved without a recommended action being taken, and $C_{action}$ is the cost of taking the recommended action (e.g., cost of clinician's time, cost of a provider match search, cost of a clinician-led chronic disease management task, cost of recommending a second opinion, etc.). The sum may be calculated over all of the user's conditions.

In some embodiments, $EV_{condition, user}$ may be the expected cost of care if the user's condition is not resolved minus the expected cost of care if the user's condition is resolved. $EV_{condition, user}$ may be calculated based on historical outcomes of similar users stored, for example, in database 106. In addition, P(need|no action, user) may be determined by building an observation cohort in two back-to-back time periods and looking at the number of users who were eligible for a recommended action in both time periods but dropped out of the observation cohort between the earlier and later time period. For example, P(need|no action, user) may be determined based on the following equation:

$$P(\text{need} | \text{no action, user}) = \frac{|C_{t1} - (C_{t1} \cap C_{t2})|}{|C_{t1}|}$$

where $C_{t1}$ is the earlier observation cohort, and $C_{t2}$ is the later observation cohort.

In some embodiments, the expected value (EV condition, user) may be avoidable emergency department cost of care, avoidable in-patient cost of care, or a combination of financial and clinical values. In some embodiments, the expected value of a recommended action may be determined using a machine learning model, such as cohort matching or a regression model. Cohort matching may be used to remove selection bias between a recommended action and a control group so that the effect of the recommended action may be determined. In calculating the expected value using cohort matching, user features may be obtained from system 100 to be used for cohort matching. In addition, differences in healthcare costs between an earlier observation cohort in a time period and a later observation cohort in the time period may be determined, and this difference may be calculated as the expected value of a recommended action.

In some embodiments, the expected value may be determined using a regression model. Regression models may be used to obtain a user personalized estimate of the expected value of resolving the user's conditions. The regression model may be trained using stored user information to predict the total healthcare costs of users meeting a particular inclusion criteria. The user features used in the regression model may comprise demographic/socioeconomic factors, comorbidities used in a matching process, or the like. The expected value of a recommended action may be determined using a regression model by applying the regression model to the user assuming the user performs the recommended action and applying the regression model to the user again while assuming the user does not perform the recommended action. The user features may be observed. The difference in the cost of care between the two estimates (e.g., assuming the user performs the recommended action and assuming the user does not perform the recommended action) may be the expected value of the recommended action for the user. The machine learning model used to determine the expected value of each recommended action may be trained using stored user information, such as healthcare data and information associated with users stored in database 106.

After determining an expected value of each of the one or more recommended actions, method 500 may proceed to step 560. In step 560, one or more processors, such as one or more processors of recommendation platform 108, may determine a rank of the one or more recommended actions based on their respective expected values. For example, one or more processors of recommendation platform 108 may rank the recommended actions in descending order so as to prioritize actions with higher expected values.

Method 500 may then proceed to step 570. In step 570, one or more processors, such as one or more processors of recommendation platform 108, may output a recommended action with a highest expected value to user 190 in response to the service request received from user 190. As discussed above, hub 204 or mobile application 205 may access the recommended action in order to display the recommended action with a highest expected value to user 190. Additionally or alternatively, one or more processors, such as one or more processors of recommendation platform 108, may output some or all of the recommended actions in the ranked order in response to the service request received from user 190. Accordingly, hub 204 or mobile application 205 may access the recommended actions in order to display the recommended actions in descending order of expected value to user 190.

Figure 6:
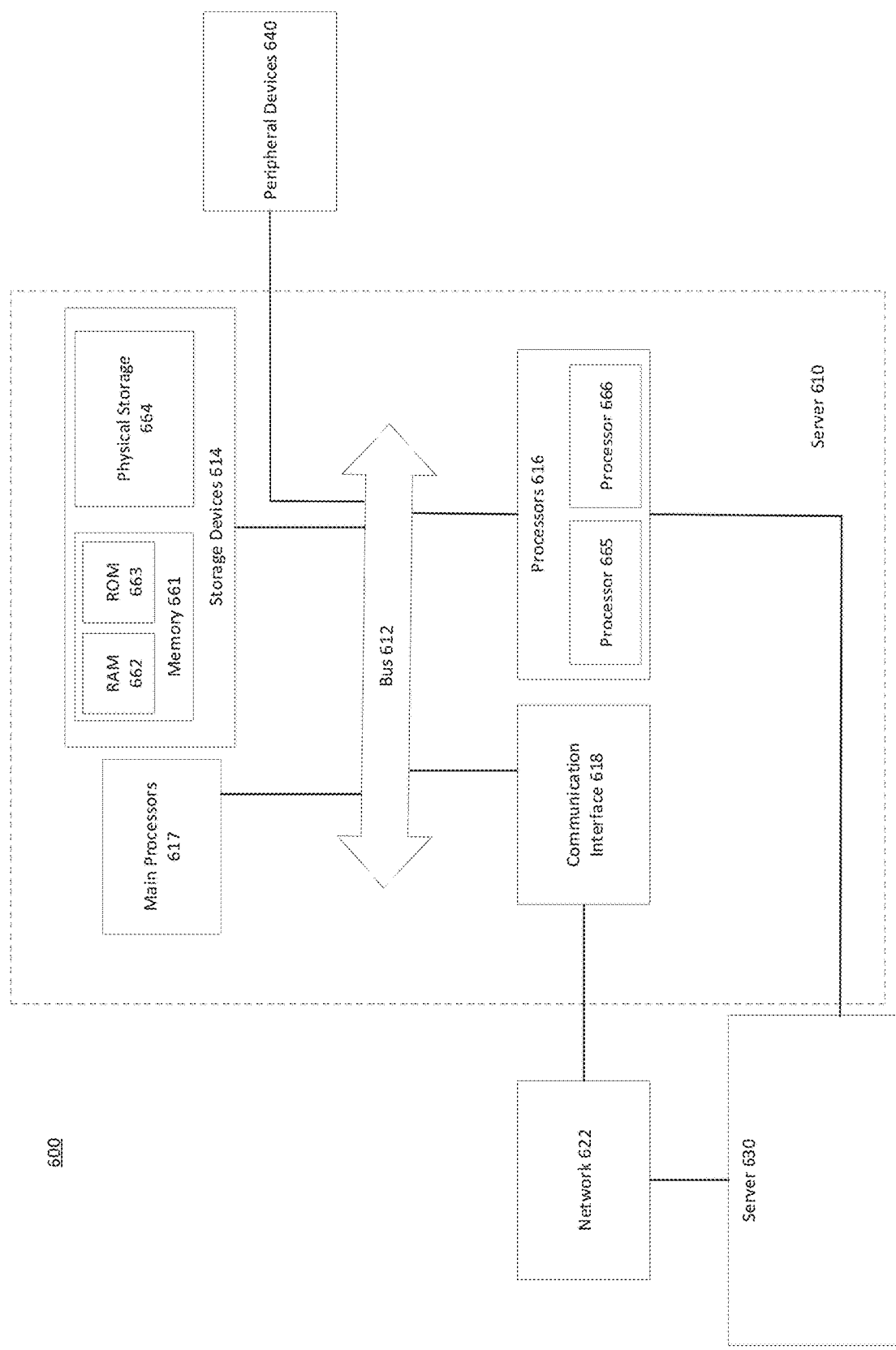
FIG. 6 illustrates a schematic diagram of an exemplary server of a distributed system, according to some embodiments of the present disclosure.

FIG. 6 illustrates a schematic diagram of an exemplary server of a distributed system, according to some embodiments of the present disclosure. According to FIG. 6, server 610 of distributed system 600 comprises a bus 612 or other communication mechanisms for communicating information, one or more processors 616 communicatively coupled with bus 612 for processing information, and one or more main processors 617 communicatively coupled with bus 612 for processing information. Processors 616 can be, for example, one or more microprocessors. In some embodiments, one or more processors 616 comprises processor 665 and processor 666, and processor 665 and processor 666 are connected via an inter-chip interconnect of an interconnect topology. Main processors 617 can be, for example, central processing units ("CPUs").

Server 610 can transmit data to or communicate with another server 630 through a network 622. Network 622 can be a local network, an internet service provider, internet, or any combination thereof. Communication interface 618 of server 610 is connected to network 622, which can enable communication with server 630. In addition, server 610 can be coupled via bus 612 to peripheral devices 640, which comprises displays (e.g., cathode ray tube (CRT), liquid crystal display (LCD), touch screen, etc.) and input devices (e.g., keyboard, mouse, soft keypad, etc.).

Server 610 can be implemented using customized hard-wired logic, one or more ASICs or FPGAs, firmware, or program logic that in combination with the server causes server 610 to be a special-purpose machine.

Server 610 further comprises storage devices 614, which may include memory 661 and physical storage 664 (e.g., hard drive, solid-state drive, etc.). Memory 661 may include random access memory (RAM) 662 and read only memory (ROM) 663. Storage devices 614 can be communicatively coupled with processors 616 and main processors 617 via bus 612. Storage devices 614 may include a main memory, which can be used for storing temporary variables or other intermediate information during execution of instructions to be executed by processors 616 and main processors 617. Such instructions, after being stored in non-transitory storage media accessible to processors 616 and main processors 617, render server 610 into a special-purpose machine that is customized to perform operations specified in the instructions. The term "non-transitory media" as used herein refers to any non-transitory media storing data or instructions that cause a machine to operate in a specific fashion. Such non-transitory media can comprise non-volatile media or volatile media. Non-transitory media include, for example, optical or magnetic disks, dynamic memory, a floppy disk, a flexible disk, hard disk, solid state drive, magnetic tape, or any other magnetic data storage medium, a CD-ROM, any other optical data storage medium, any physical medium with patterns of holes, a RAM, a PROM, and an EPROM, a FLASH-EPROM, NVRAM, flash memory, register, cache, any other memory chip or cartridge, and networked versions of the same.

Various forms of media can be involved in carrying one or more sequences of one or more instructions to processors 616 or main processors 617 for execution. For example, the instructions can initially be carried out on a magnetic disk or solid-state drive of a remote computer. The remote computer can load the instructions into its dynamic memory and send the instructions over a telephone line using a modem. A modem local to server 610 can receive the data on the telephone line and use an infra-red transmitter to convert the data to an infra-red signal. An infra-red detector can receive the data carried in the infra-red signal and appropriate circuitry can place the data on bus 612. Bus 612 carries the data to the main memory within storage devices 614, from which processors 616 or main processors 617 retrieves and executes the instructions.

The adaptive weighting system 100 one or more of its components may reside on either server 610 or 630 and may be executed by processors 616 or 617. In some embodiments, the components of the adaptive weighting system 100 may be spread across multiple servers 610 and 630. For example, the online ranking service instances 211-214 may be executed on multiple servers. Similarly, the in-memory database instances 331-333 may be maintained by multiple servers 610 and 630.

Figure 7A:
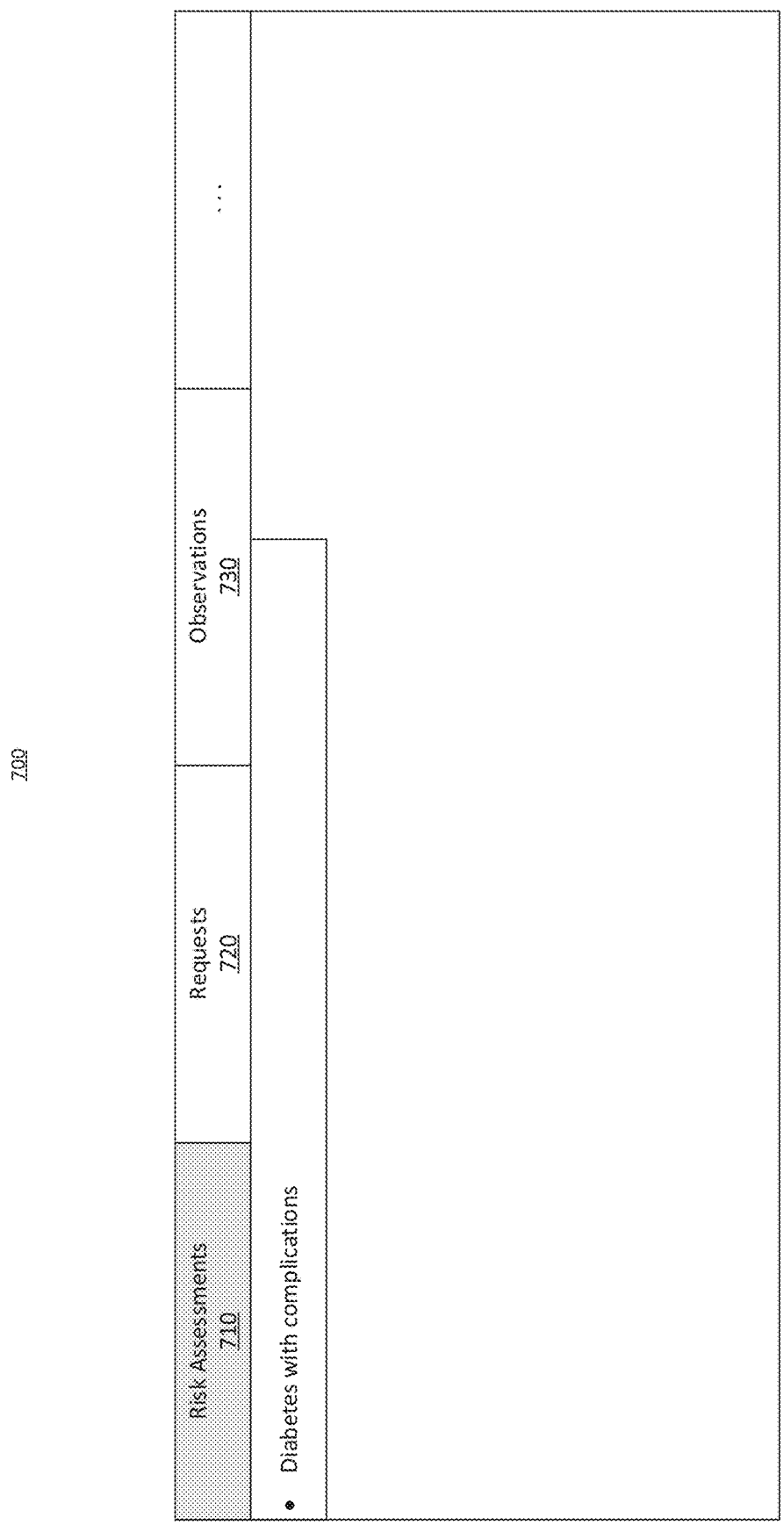
FIG. 7A illustrates an exemplary user interface for providing personalized action recommendation, according to some embodiments of the present disclosure.

FIGS. 7A-7C illustrate an exemplary user interface 700 for providing personalized action recommendation, according to some embodiments of the present disclosure. A user, such as user 190, may access various information associated with a patient, including but not limited to, risk assessments 710, requests 720, and observations 730. A user may comprise, for example, a patient, an insurance provider, a marketer, a care coordinator, or a clinician. As show in FIG. 7A, the user may view risk assessments 710 associated with a patient, which may be indicative of health risks, needs, or conditions of the patient (e.g., patient is suffering from diabetes with complications that may exacerbate the patient's condition).

In some embodiments, the user may access requests 720 associated with the user. As shown in FIG. 7B, for example, user interface 700 may display a list of past and present requests 721, a request group 722 associated with the request 721, any notes 723 associated with the request 721, priority level 724 of the request 721, and status information 725 of the request 721. For example, after identifying the conditions or needs of a patient, a list of requests 721 (e.g., pharmacist referral, eye exam, primary care physician (PCP) referral, etc.) may be generated to resolve the conditions or needs of the patient. The requests 721, for example, may be a personalized recommended action for the patient to resolve the conditions or needs of the patient. The requests 721 may be entered by a member of a group 722, including but not limited to insurance providers, certified compliance professional (CCP), the user, or the like. In some embodiments, a member of the group 722 associated with the request 721 may be responsible for completing the request 721. In other embodiments, user interface 700 may display notes 723 associated with the request 721 in order to display any explanation or reasoning for entering the request 721 to resolve the conditions or needs of the patient.

User interface 700 may also display a priority level 724 associated with the request 721. Priority level 724 may be based on an expected value of each recommended action associated with the request 721. For example, as shown in FIG. 7B, an expected value for a pharmacist referral may be higher than an expected value for an eye exam for a specific patient. In addition, an expected value for an eye exam may be higher than an expected value for a PCP referral for the specific patient. As such, the priority level of a PCP referral may be lower than that of an eye exam, which may be lower than a priority level of a pharmacist referral. The requests 721 may be ranked and displayed by their priority levels 724 in descending order. As such, requests 721 with the highest priority level (e.g., priority level of 1) may be displayed first and requests 721 with the lower priority level (e.g., priority level of 3) may be displayed last. Accordingly, the user may be able to view easily and readily the most urgent (e.g., highest priority) requests 721 first on user interface 700. In other embodiments, user interface 700 may display a status information 725 associated with each request 721 in order to view easily and readily the requests 721 that have been completed and that are pending or require immediate attention.

In some embodiments, user interface 700 may display observations 730 associated with a patient, such as illustrated in example user interface 700 of FIG. 7C. For example, user interface 700 may display a list of observations 731, category 732 associated with the observation 731, and any notes 733 associated with the observation 731. Observations 731 may refer to information about the patient that can be learned or inferred from, for example, healthcare data and information associated with the user, such as low medication adherence, lack of valid eye exam in the past year, or low quality PCP. Observations 731 may be organized into different categories 732, such as medication adherence category, diabetes best practice category, or provider quality category. By organizing observations 731 into categories 732, a recommendation platform, such as recommendation platform 108, may be able to easily categorize the patient into a segment, determine the type of conditions or needs associated with the patient, identify features associated with the patient, and recommend actions for the patient. In addition, notes 733 associated with each observation 731 may comprise any explanation or reasoning associated with each observation 731. Notes 733 may, for example, provide more information associated with each observation 731 in order to better identify the conditions or needs of the patient, as well as actions to recommend to resolve the conditions or needs of the patient.

As used herein, unless specifically stated otherwise, the term "or" encompasses all possible combinations, except where infeasible. For example, if it is stated that a component may include A or B, then, unless specifically stated otherwise or infeasible, the component may include A, or B, or A and B. As a second example, if it is stated that a component may include A, B, or C, then, unless specifically stated otherwise or infeasible, the component may include A, or B, or C, or A and B, or A and C, or B and C, or A and B and C.

Example embodiments are described above with reference to flowchart illustrations or block diagrams of methods, apparatus (systems) and computer program products. It will be understood that each block of the flowchart illustrations or block diagrams, and combinations of blocks in the flowchart illustrations or block diagrams, can be implemented by computer program product or instructions on a computer program product. These computer program instructions may be provided to a processor of a computer, or other programmable data processing apparatus to produce a machine, such that the instructions, which execute via the processor of the computer or other programmable data processing apparatus, create means for implementing the functions/acts specified in the flowchart or block diagram block or blocks.

These computer program instructions may also be stored in a computer readable medium that can direct one or more hardware processors of a computer, other programmable data processing apparatus, or other devices to function in a particular manner, such that the instructions stored in the computer readable medium form an article of manufacture including instructions that implement the function/act specified in the flowchart or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions that execute on the computer or other programmable apparatus provide processes for implementing the functions/acts specified in the flowchart or block diagram block or blocks Any combination of one or more computer readable medium(s) may be utilized. The computer readable medium may be a non-transitory computer readable storage medium. In the context of this document, a computer readable storage medium may be any tangible medium that can contain or store a program for use by or in connection with an instruction execution system, apparatus, or device.

Program code embodied on a computer readable medium may be transmitted using any appropriate medium, including but not limited to wireless, wireline, optical fiber cable, RF, IR, etc., or any suitable combination of the foregoing.

Computer program code for carrying out operations for example embodiments may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flowchart and block diagrams in the figures illustrate examples of the architecture, functionality, and operation of possible implementations of systems, methods, and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts, or combinations of special purpose hardware and computer instructions.

It is understood that the described embodiments are not mutually exclusive, and elements, components, materials, or steps described in connection with one example embodiment may be combined with, or eliminated from, other embodiments in suitable ways to accomplish desired design objectives.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the invention disclosed herein. It is intended that the specification and examples be considered as exemplary only. It is also intended that the sequence of steps shown in figures are only for illustrative purposes and are not intended to be limited to any particular sequence of steps. As such, those skilled in the art can appreciate that these steps can be performed in a different order while implementing the same method.

What is claimed is:

1. A non-transitory computer readable medium including instructions that are executable by one or more processors to cause a system to perform a method for generating a personalized action recommendation, the method comprising:
    acquiring a request for a service from a first user, wherein the request is associated with a second user and the second user's condition;
    receiving user information from a plurality of data sources in a plurality of formats;
    converting the received user information into a bundle by normalizing the received user information in the plurality of formats to a consistent format and mapping the normalized user information to a plurality of aspects of the bundle;
    storing the converted user information;
    identifying one or more features of the second user based on the stored user information;
    assigning the second user to two or more segments of users based on the identified one or more features, wherein assigning the second user to the segment two or more segments comprises determining confidence values of the two or more segments;
    generating a set of two or more recommended actions for the second user based on the two or more segments;
    determining an expected value of each of the two or more recommended actions based on a probability of the second user performing the two or more recommended actions;
    determining a rank of the two or more recommended actions based on the expected value of each of the two or more recommended actions; and
    outputting a recommended action to the first user with a highest expected value for the second user in response to the request for the service.

2. The non-transitory computer readable medium of claim 1, wherein the expected value of each of the two or more recommended actions is determined based on an expected value of resolving the second user's condition, a probability that the two or more recommended actions resolves the second user's condition, a probability that the second user's condition is resolved without the two or more recommended actions, and a cost of taking the two or more recommended actions.

3. The non-transitory computer readable medium of claim 2, wherein the expected value of resolving the second user's condition is determined by subtracting an expected cost of care if the second user's condition is resolved from an expected cost of care if the second user's condition is not resolved.

4. The non-transitory computer readable medium of claim 1, wherein the expected value of each of the two or more recommended actions is determined using a machine learning model.

5. The non-transitory computer readable medium of claim 4, wherein the machine learning model comprises at least one of cohort matching or a regression model.

6. The non-transitory computer readable medium of claim 4, wherein the machine learning model is trained using the stored user information.

7. The non-transitory computer readable medium of claim 1, wherein the one or more features comprise a state of the second user, and wherein the state of the second user comprises at least one of a gap in care, a medical condition, medications, attributes, behaviors, genetics data, or social determinants of health associated with the second user.

8. The non-transitory computer readable medium of claim 1, wherein the one or more features comprise a goal associated with the second user, and wherein the goal associated with the second user is extrapolated based on stored medical history of the second user.

9. The non-transitory computer readable medium of claim 1, wherein:
    the second user is a patient;
    the request for the service is from the first user comprising at least one of a marketer, a care coordinator, or a clinician.

10. The non-transitory computer readable medium of claim 1, wherein the two or more segments of users comprise a set of users who share at least one of the one or more features or the second user's condition.

11. A method performed by a system for generating a personalized action recommendation, the method comprising:
    acquiring a request for a service from a first user, wherein the request is associated with a second user and the second user's condition;
    receiving user information from a plurality of data sources in a plurality of formats;
    converting the received user information into a bundle by normalizing the received user information in the plurality of formats to a consistent format and mapping the normalized user information to a plurality of aspects of the bundle;
    storing the converted user information;
    identifying one or more features of the second user based on the stored user information;
    assigning the second user to two or more segments of users based on the identified one or more features, wherein assigning the second user to the two or more segments comprises determining confidence values of the two or more segments value of the segment;
    generating a set of two or more recommended actions for the second user based on the two or more segments;

determining an expected value of each of the two or more recommended actions based on a probability of the second user performing the two or more recommended actions;

determining a rank of the two or more recommended actions based on the expected value of each of the two or more recommended actions; and outputting a recommended action to the first user with a highest expected value for the second user in response to the request for the service.

12. The method of claim 11, wherein the expected value of each of the two or more recommended actions is determined based on an expected value of resolving the second user's condition, a probability that the two or more recommended actions resolves the second user's condition, a probability that the second user's condition is resolved without the two or more recommended actions, and a cost of taking the two or more recommended actions.

13. The method of claim 12, wherein the expected value of resolving the second user's condition is determined by subtracting an expected cost of care if the second user's condition is resolved from an expected cost of care if the second user's condition is not resolved.

14. The method of claim 11, wherein the expected value of each of the two or more recommended actions is determined using a machine learning model, and wherein the machine learning model comprises at least one of cohort matching or a regression model.

15. The method of claim 14, wherein the machine learning model is trained using the stored user information.

16. The method of claim 11, wherein the one or more features comprise a state of the second user, and wherein the state of the second user comprises at least one of a gap in care, a medical condition, medications, attributes, behaviors, genetics data, or social determinants of health associated with the second user.

17. The method of claim 11, wherein the one or more features comprise a goal associated with the second user, and wherein the goal associated with the second user is extrapolated based on stored medical history of the second user.

18. The method of claim 11, wherein:
the second user is a patient;
the request for the service is from the first user comprising at least one of a marketer, a patient, a care coordinator, or a clinician.

19. The method of claim 11, wherein the two or more segments of users comprises a set of users who share at least one of the one or more features or the second user's condition.

20. A personalized action recommendation system comprising:
one or more memory devices storing processor-executable instructions; and
one or more processors configured to execute the instructions to cause the personalized action recommendation system to perform:
acquiring a request for a service from a first user, wherein the request is associated with a second user and the second user's condition;
receiving user information from a plurality of data sources in a plurality of formats;
converting the received user information into a bundle by normalizing the received user information in the plurality of formats to a consistent format and mapping the normalized user information to a plurality of aspects of the bundle;
storing the converted user information;
identifying one or more features of the second user based on the stored user information;
assigning the second user to two or more segments of users based on the identified one or more features, wherein assigning the second user to the two or more segments comprises determining confidence values of the two or more segments;
generating a set of two or more recommended actions for the second user based on the two or more segments;
determining an expected value of each of the two or more recommended actions based on a probability of the second user performing the two or more recommended actions;
determining a rank of the two or more recommended actions based on the expected value of each of the two or more recommended actions; and
outputting a recommended action to the first user with a highest expected value for the second user in response to the request for the service.

* * * * *